United States Patent [19]

Hood, Jr. et al.

[11] Patent Number: 4,461,266
[45] Date of Patent: Jul. 24, 1984

[54] ADAPTIVE INCREMENTAL BLOOD PRESSURE MONITOR

[75] Inventors: Rush W. Hood, Jr., Tampa; Richard Medero, Lutz, both of Fla.

[73] Assignee: Critikon, Inc., Tampa, Fla.

[21] Appl. No.: 373,209

[22] Filed: Apr. 29, 1982

[51] Int. Cl.³ .............................................. A61B 5/02
[52] U.S. Cl. .................................... 128/681; 128/680; 128/677
[58] Field of Search ................. 128/672, 677, 680–683

[56] References Cited

U.S. PATENT DOCUMENTS

| | | | |
|---|---|---|---|
| 2,826,191 | 3/1958 | Burns | 128/682 |
| 3,903,872 | 9/1975 | Link | 128/681 |
| 4,009,709 | 3/1977 | Link et al. | 128/681 |
| 4,074,711 | 2/1978 | Link et al. | 128/681 |
| 4,106,498 | 8/1978 | Haney | 128/681 |
| 4,137,907 | 2/1979 | Jansen et al. | 128/681 |
| 4,140,110 | 2/1979 | Jansen et al. | 128/681 |
| 4,154,238 | 5/1979 | Link | 128/681 |
| 4,174,707 | 11/1979 | Link et al. | 128/681 |
| 4,223,681 | 9/1980 | Sherman | 128/672 |
| 4,271,843 | 6/1981 | Flynn | 128/681 |
| 4,273,136 | 6/1981 | Kubo et al. | 128/680 |
| 4,349,034 | 9/1982 | Ramsey | 128/682 X |
| 4,378,807 | 4/1983 | Peterson et al. | 128/682 X |

Primary Examiner—Lee S. Cohen
Assistant Examiner—Angela D. Sykes
Attorney, Agent, or Firm—Audley A. Ciamporcero, Jr.

[57] ABSTRACT

An adaptive monitor and method for rapidly determining blood pressure, selects an initial cuff pressure to be applied to an artery of the test subject and then measures the amplitude of pressure pulses caused by the pumping of blood by the subject's heart. The cuff pressure is incrementally increased while the pulse amplitudes are monitored in order to obtain blood pressure readings by the oscillometric method. If the pulse amplitudes decrease for increases in pressure above the initial value, it is taken as an indication that mean arterial pressure is below the initial cuff pressure. Thus the cuff pressure is substantially decreased to a new initial value and the process is restarted. If it should be found upon a determination of the mean arterial pressure and the systolic pressure, that the initial or new cuff pressure was not low enough to determined diastolic pressure, the cuff pressure is automatically decreased in one large step to a level below the initial pressure and is then decreased in steps until diastolic pressure is located.

11 Claims, 9 Drawing Figures

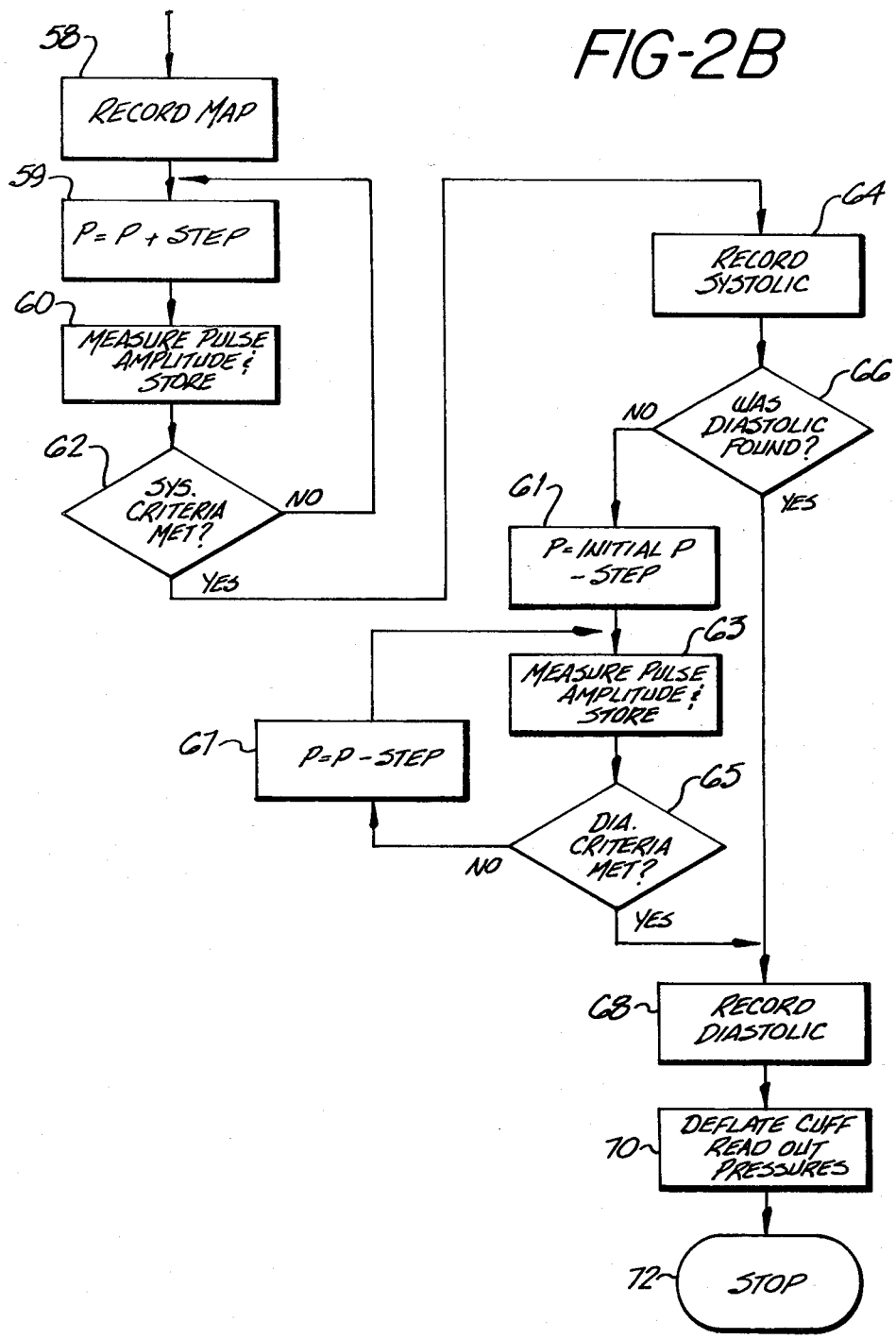

ADAPTIVE INCREMENTAL BLOOD PRESSURE MONITOR

FIELD OF THE INVENTION

This invention relates to the automated measurement of blood pressure and, more particularly, to the automated measurement of blood pressure by the oscillometric method.

BACKGROUND AND PRIOR ART

The heart muscles of animals periodically contract to force blood through the arteries of the animal. As a result, irregularly-shaped pressure pulses exist in these arteries and cause them to flex or oscillate. The base line pressure for these pulses is known as the diastolic pressure and the peak pressure for these pulses is known as the systolic pressure A further pressure value, known as the "mean arterial pressure" (MAP), represents a time-weighted average of the pulse pressure. In the past, various techniques and devices have been used for measuring one or more of these blood pressure values. The most common method involves applying a pressure cuff about the upper arm of a test subject and inflating it so as to stop the flow of blood in the brachial artery. The pressure is then slowly relieved while a stethoscope is used on the distal portion of the artery to listen for pulsating sounds, known as Korotkoff sounds, that accompany the reestablishment of blood flow in the artery. As the pressure in the cuff is reduced further, the Korotkoff sounds eventually disappear. The cuff pressure at which the Korotkoff sounds first appear during deflation of the cuff is a measure of the systolic pressure and the pressure at which these sounds disappear is a measure of the diastolic pressure. This method of blood pressure detection is generally known as the ausculatory method.

Various devices are well known in the prior art for automatically performing blood pressure measurements by the ausculatory method. These devices employ a pump to automatically inflate a pressure cuff and a microphone to convert the Korotkoff sounds into electrical signals which are easily detected by various types of circuits. Other techniques have also been used to detect blood pressure from outside the subject's body, e.g., via Doppler shifts in ultrasonic waves reflected by the artery wall. In addition, there are intrusive devices that are inserted directly into the blood vessels for measurement of the pressure. However, the most commonly used method for measuring blood pressure, other than the ausculatory method, is the oscillometric method.

The oscillometric technique is based on the fact that the pumping of blood through the arteries by the heart causes the arteries to flex. Even in the area adjacent to or within a pressure cuff applied to the arm of a test subject, these pressure variations exist. In fact they will pass from the artery through the arm of the test subject and into the pressure cuff itself. While these pressure variations are small compared to the typical pressure applied by the cuff, they are nevertheless detectable by a transducer located to measure the pressure within the cuff. It has been found that these pulses have a peak-to-peak amplitude which is minimal for applied cuff pressures above the systolic pressure and below the diastolic pressure. The amplitude of these pulses, however, rises to a maximum value at a cuff pressure equivalent to the mean arterial pressure. It has further been found that the pulse amplitudes for cuff pressures equivalent to the systolic and diastolic pressures have a fixed relationship to the pulse amplitude at the mean arterial pressure. Thus the oscillometric method is based on measurements of detected pulse amplitudes at various cuff pressures.

Automated blood pressure measuring devices operating according to the oscillometric method have been proposed in which the peak-to-peak amplitude of the pressure pulsations are detected at various applied cuff pressures. The amplitudes of these pulses, as well as the applied cuff pressure, are stored together as the device automatically changes the cuff pressure over the range of interest. Then the peak-to-peak amplitudes are evaluated to find the maximum and its related cuff pressure, which is designated the mean arterial pressure (MAP). The cuff pressure below MAP which produces a peak-to-peak pulse amplitude having a certain fixed relationship to the peak-to-peak value at MAP, is designated as the diastolic pressure. Likewise, the equivalent cuff pressure above MAP which results in pulsations having an amplitude with a certain fixed relationship to that at MAP, is designated as the systolic pressure. In modifications of this basic oscillometric technique, derivatives of the pulse wave forms are taken and maximums of the derivatives are used as indications of the occurrence of the systolic and diastolic pressures. The relationships of systolic and diastolic pressures, respectively, to MAP, are empirically derived ratios which assume varying levels depending on the preferences of those of ordinary skill in the art. Generally, these pressures are calculated in the range of 30 to 70% of MAP.

In many situations, the speed with which blood pressure readings are taken is not critical, although a delay in making a measurement may represent an inconvenience to the test subject. However, in certain situations, for example, during surgery or during the emergency treatment of patients who have suffered severe trauma, it is often necessary to obtain the blood pressure reading quickly and to obtain repeated readings over a period of time. With the automatic oscillometric blood pressure devices known from the prior art, the cuff pressure is either increased in increments until the desired readings are obtained (an incrementing device) or it is rapidly brought to a high pressure, which is thought to be above systolic pressure, and then decreased in increments (decrementing device). Since normal blood pressure lies in the range between about 70 and 120 millimeters of mercury, one technique for improving the speed with which the blood pressure readings can be taken is to start with a reasonably high value of initial pressure, for example, 50 to 70 millimeters of mercury, when an incrementing device is used. Similarly a decrementing device could start with a relatively low pressure with respect to systolic, for example, 120 to 140 millimeters of mercury. Thus, the portions of the pressure range where it is unlikely that useful information will be obtained are skipped over and the measurement speed is increased.

The difficulty with skipping part of the pressure range to speed up the process is that a person in shock may have such a low blood pressure that the automated operation may completely miss significant information, e.g. the diastolic pressure. Likewise, if a person is suffering from arterial disease, his blood pressure may be extremely high and a decrementing device with too low an initial cuff pressure may not detect the systolic pressure. Besides the people with heart disease or who are in shock, certain people naturally have blood pressures outside the normal range. Typical of this is the blood pressure of long distance runners which tends to be much lower than that of the general population. With such people, a blood pressure reading may not be possible with a device in which part of the pressure range is skipped in order to obtain faster readings.

Of course, a skilled operator, upon failing to get a reading, can reset the machine to search for blood pressure in a lower or higher range as indicated. However, in critical situations in which speed is of the essence, this may not be accomplished easily. In particular, the operator may assume that the failure to read a blood pressure is due to a failure of the machine, as opposed to an abnormally high or low pressure in the test subject. Thus, valuable time may be lost in trying to check out the equipment. Further during emergency treatment or surgery, it may not be convenient for the operator, for example, a paramedic or an anesthesiologist, to reprogram the machine since he may be engaged in other critical life saving operations.

DISCLOSURE OF THE INVENTION

The present invention is directed to a method and apparatus for quickly, accurately and automatically determining the blood pressure of a test subject even when that subject's blood pressure is outside the normal expected range. This object is achieved by having the blood pressure device or monitor operate in an adaptive mode in which it initially moves to the normal range of expected blood pressure and begins to take readings. Should these readings show that the actual blood pressure values of the test subject are outside the normal range, it automatically calculates the direction in which the cuff pressure must change in order to get a reading and then adapts its operation to obtain the reading.

In an illustrative embodiment of the invention, blood pressure measurements are taken by equipment adapted to operate in the oscillometric manner. In particular, a pressure cuff located about an artery of the test subject is automatically inflated to a predetermined value located near the bottom of the normal blood pressure range for diastolic pressure. The cuff pressure is then automatically incremented while the amplitude of pressure pulses received from the artery are measured and stored along with the applied cuff pressure. As the cuff pressure is increased in increments, the pulse amplitudes for a normal subject should also increase in amplitude as the mean arterial pressure is approached. If after a few increments, it is clear that the pulse amplitudes are decreased, indicating that the cuff pressure is already beyond the mean arterial pressure, a large decrease in the applied cuff pressure is made and pulse amplitudes at increasing increments from the new level are again measured. Should it be detected that the pulse amplitudes are again decreasing for increasing increments of cuff pressure, a further large decrease in cuff pressure will be made.

When the cuff pressure is finally below the mean arterial pressure, such that increasing increments will result in increases in the amplitudes of the pulses, the cuff pressure is made to continue to increment until the maximum peak-to-peak amplitude is detected. The cuff pressure where this occurs is designated as the mean arterial pressure (MAP). The applied cuff pressure is then made to further increment above MAP until the peak-to-peak pulse amplitudes decrease to a certain fixed fraction of the amplitude at MAP. The applied cuff pressure at this point is designated as the systolic pressure. Next, the data obtained for cuff pressures below MAP is reviewed to find the cuff pressure which is related to a pulse amplitude equal to a fixed fraction of the pulse amplitude at MAP. This applied cuff pressure is designated the diastolic pressure. Once the device has determined that all of the necessary pressure readings have been made, the cuff is rapidly deflated, relieving the applied pressure.

Should the review of the data obtained at cuff pressures below MAP indicate that the diastolic pressure was not detected, rather than deflating the cuff pressure to zero, it is relieved enough to reduce it to the initial pressure with which the sucessful measurement of MAP was made. Then the cuff pressure is decremented until the diastolic pressure is located.

With the present invention, the search for the relevant blood pressure values of the test subject occurs automatically, in a relatively short period of time and without the intervention of the operator. Thus the operator need not be distracted from life saving operations to recalibrate the blood pressure monitor. In addition, the operator is relieved of the necessity of making a decision as to whether the equipment is working properly or whether the blood pressure is outside the normal range. The machine automatically searches for the proper blood pressure values.

In a situation in which repeated blood pressure readings are to be made, the device can be made to retain values from the previous calculations to use as starting values for a new indication. Thus, the machine will adapt itself to the blood pressure ranqe detected from the test subject during repeated tests for this information.

BRIEF DESCRIPTION OF THE DRAWINGS

The foregoing and other features of the present invention will be more readily apparent from the following detailed description and drawings of an illustrative embodiment of the invention in which.

DETAILED DESCRIPTION OF THE INVENTION

Figure 1:
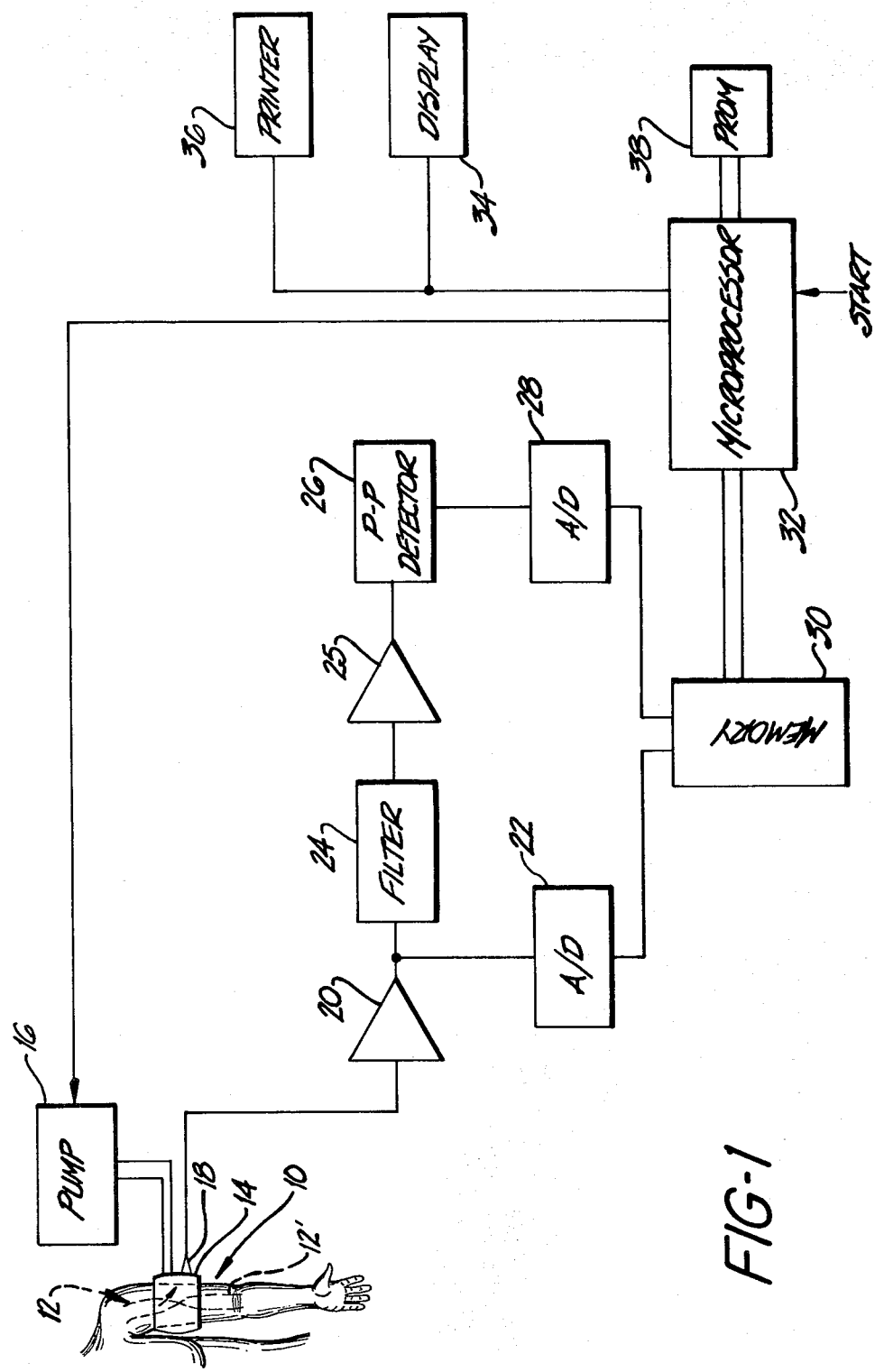
FIG. 1 is a block diagram of apparatus suitable for carrying out the present invention.

In FIG. 1 there is shown the arm 10 of a test subject with a pressure cuff 14 located about the upper portion thereof such that it can occlude the brachial artery 12 upon inflation. Pressure to inflate the cuff is derived from a pump 16. In the state shown in FIG. 1, the pressure in the cuff is just sufficient to occlude the brachial artery, i.e. it is at the systolic pressure. Thus, there is no blood flow in the distal portion 12' of the artery, but the action of the test subject's heart still causes pressure pulsations or vibrations in the portion of the artery above the occlusion, which pulsations are transmitted into the cuff as shown by the arrow. These pressure pulses, as well as the pressure from pump 16, are detected by transducer 18 and converted into an electrical signal.

Typically, the maximum pressure of the cuff is applied at its midpoint as shown in FIG. 1 at the location where the artery is blocked. Thus, at a systolic pressure, half of the arterial area within the cuff is pulsating and the other half is not. Thus, the amplitude of pulses at systolic pressure is typically in the range of one-half the amplitude of the pulses at MAP where the entire artery is pulsating. This gives rise to the fixed fractional value of pulse amplitude used to calculate systolic pressure. At values below MAP, the constriction from the cuff is lowered such that the pulsation amplitudes are also lower. It has been found that at diastolic pressure, the pulse amplitudes are also a fixed fraction of the MAP pulse amplitude.

In order to be able to detect high systolic pressures, which may be representative of heart disease, while still applying only the minimum necessary cuff pressure to the arm of the test subject, the present invention is generally of the incrementing type which applies a low cuff pressure and then increments the cuff pressure to higher values in order to obtain the necessary blood pressure readings. Thus, as soon as the systolic pressure is obtained, the cuff can be deflated. In prior art decrementing devices in which the cuff is automatically inflated to a level well above the expected systolic pressure, an undue amount of pressure is applied to the arm of the test subject. This pressure, which may result in pain and even damage to the arm of the test subject, is generally avoided with the present invention.

Figure 3A:
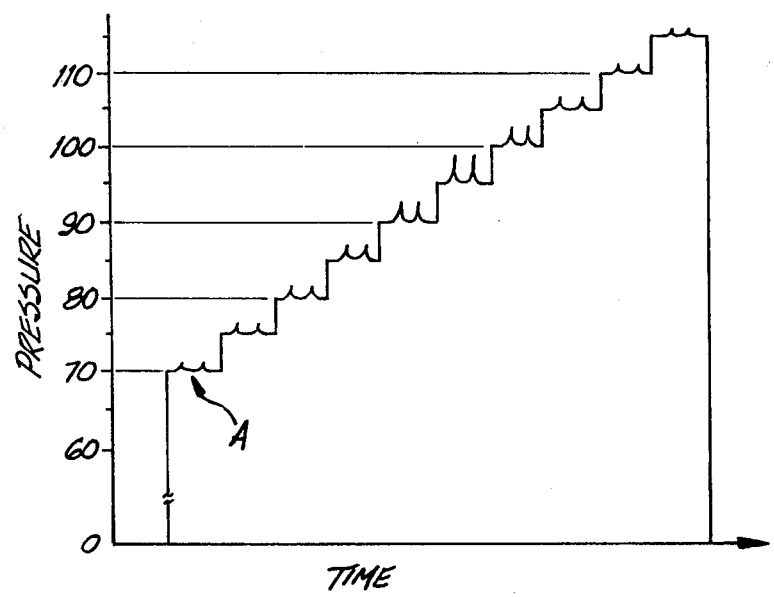
FIGS. 3a and 3b are graphs of the cuff pressure and pulse amplitudes, respectively, for a test subject having a normal blood pressure range.
Figure 3B:
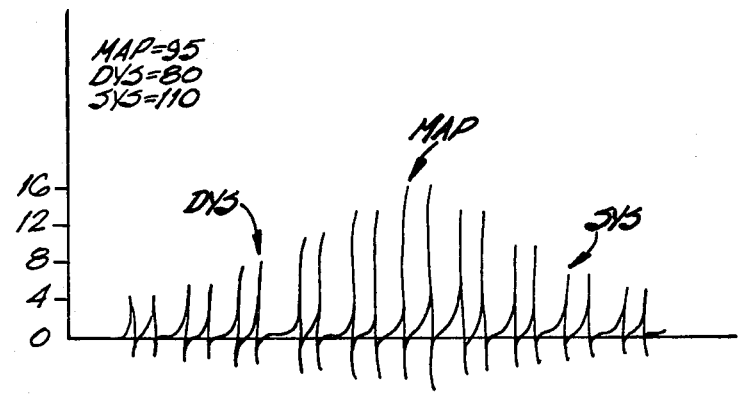

In order to obtain a rapid reading of blood pressure, the pump 16 applies an initial cuff pressure which is just below the expected range of diastolic pressures for normal subjects, for example 60 or 70 millimeters of mercury. At this pressure, transducer 18 will receive a pressure signal which is a summation of the applied cuff pressure and the pulsations created by blood flow through the brachial artery 12. The signal obtained at this point is the first level A shown in FIG. 3a. Transducer 18 converts this pressure signal into an electrical signal which is amplified by amplifier 20 and applied both to an analog-to-digital converter 22 and a band pass filter 24. Converter 22 generates a digital signal representative of the output of the transducer. Since the pulsations are such a relatively small portion of this signal, as shown in FIG. 3a wherein the amplitude of the pulses is even exaggerated, the digital output of circuit 22 generally represents only the applied cuff pressure. Filter circuit 24 eliminates the d.c. portion of the signal which is related to the applied cuff pressure and passes only the pulses. These pulses are then amplified in amplifier 25 and transmitted to a peak-to-peak detector 26. FIG. 3b is a graph of the amplified signal leaving amplifier 25 for various levels of applied cuff pressure.

Peak-to-peak detector 26 generates an output analog signal related to the peak-to-peak amplitude of the pulses. These analog signals are then converted into a digital signal in analog-to-digital converter 28. Both the digital signal related to cuff pressure and the digital signal related to the peak-to-peak pulse amplitudes are stored together in a memory circuit 30 for later use in determining blood pressure.

In a typical case, which is also representative of the prior art, the initial applied cuff pressure is incremented in steps, for example 5 millimeters of mercury, and the peak-to-peak amplitude of the pulses at each increment is detected. This operation is repeated until all of the necessary information to determine the relevant blood pressures is completed, for example, as shown in FIG. 3a and 3b. In FIG. 3b, it can be seen that the amplitudes of the pulses increase for each increase in cuff pressure until a maximum is reached. Then they begin to decrease. The mean arterial pressure is equivalent to the cuff pressure at which the maximum pulse amplitude exist. In addition, the systolic pressure is equal to the applied cuff pressure above MAP at which the pulse amplitude is some predetermined fraction of that at MAP. Likewise, the diastolic pressure is that cuff pressure below MAP at which the peak-to-peak amplitudes of the pulses are a predetermined fraction of that at MAP.

If for some reason the test subject has a blood pressure such that the diastolic pressure is below the predetermined fixed start up cuff pressure, i.e. 70 mm Hg, the device according to the present invention will operate as shown by the graphs in FIGS. 4a and 4b. In particular, the cuff pressure will be initially inflated and the pulse amplitude will be measured at various increments until MAP is determined (B in FIG. 4a). The cuff pressure continues to be incremented as the pulse amplitudes are reduced above MAP until the systolic pressure reading is obtained (C in FIG. 4a). An additional increment and measurement may be made in order to make sure that the systolic pressure has been reached, but this is optional. At this point, the device reviews the pressure data prior to the occurrence of MAP to see if the value for diastolic pressure has been obtained. In this case, it has not. Therefore, the cuff pressure is deflated in one step to a value equal to the original starting pressure of 70 mm Hg minus one step (D in FIG. 4a) and a measurement is made. If this does not represent diastolic pressure, the pressure is decremented in steps and measurements are made until the diastolic reading is obtained (E in FIG. 4a).

If the patient is in shock, his blood pressure readings may be so low that the initial increment of cuff pressure may be above both the diastolic and MAP levels. This situation is illustrated in FIGS. 5a where the scale of applied pressure has been changed from that in FIGS. 3a and 4a. By comparing the pulse amplitudes in FIG. 5b for the initial cuff pressure and the first increment, it can be seen that the pulse levels are decreasing (F in FIG. 5b), thereby indicating that the cuff pressure is above MAP. To compensate for this, a large drop in cuff pressure is initiated, for example, a decrease of 50 mm Hg. Once this decrease has been accomplished, the incrementing of the cuff pressure begins again in search for the selected blood pressure values. In practice, it may be found that the drop of 50 mm Hg is too great. Therefore, any other convenient pressure drop can be utilized, for example, a drop of 25 mm Hg as shown at G in FIG. 5a. If a smaller drop in pressure is used and the pressure is still not low enough to be below MAP, this will be detected by a decrease in pulse amplitude with increasing cuff pressure. As a result, the cuff pressure can again be reduced by an increment of, for example, 25 mm Hg. As soon as the situation is reached in which the cuff pressure and pulse amplitude increase together, the system will operate in the ordinary manner to determine the diastolic mean arterial and systolic pressures.

Regardless of the adaptive manner in which the device determines blood pressure for the first time, this value can then be retained and used as a starting point in calculating blood pressure during subsequent periods of time. For example, if a patient is in intensive care and needs to have his blood pressure taken every 5 minutes, the initial cuff pressure can be arranged to be 15 mm Hg below the previously-determined diastolic pressure.

The operation of the device, including the control of the cuff pressure and the determination of the pressure values from the information stored in memory 30, may be under the direction of a microprocessor 32 (FIG. 1). This processor 32 will also act to deliver the pressure values to an output device, e.g. a display 34, for use by the operator. In addition, the output may be permanently recorded on a paper tape printer 36 or some other medium so that comparisons over a period of time can be made easily. Operation of the microprocessor so that the monitor works according to the present invention, is by means of a program stored, for example, in PROM 38.

Figure 2A:
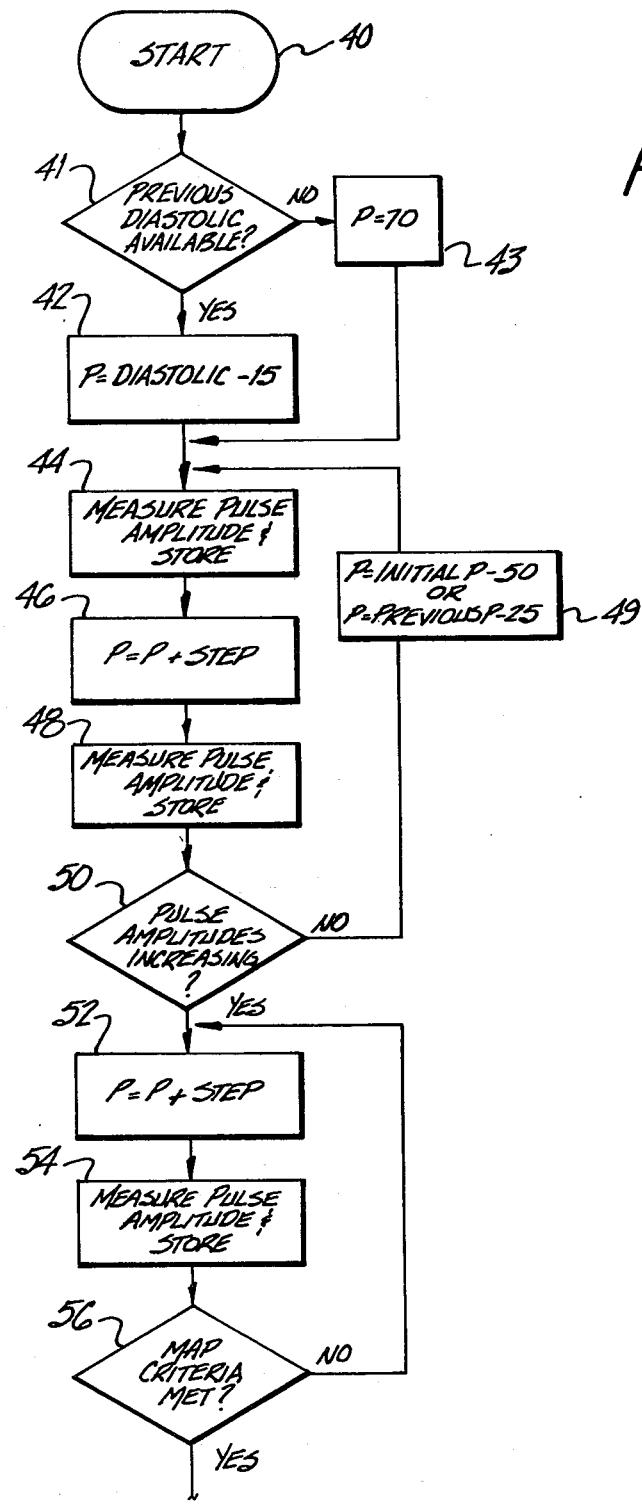
FIG. 2 is a flow chart for a program for the processor of FIG. 1 which exemplifies the method of the present invention.

In FIG. 2, there is shown a flow chart which describes the operation of the apparatus set forth in FIG. 1 and provides the basis for the program of the processor 32 which is stored in PROM 38. When the start button of the machine is pressed, the circuits are reset at step 40 and then the decision at step 41 is made. This decision determines whether or not a previous diastolic pressure level is available. If there is a previous level, the initial pressure for the cuff is set in step 42 to a pressure equal to that diastolic pressure minus 15 mm Hg. If there is no previous reading, the cuff pressure is set in step 43 to an arbituary predetermined value, for example 60 or 70 mm Hg. Once the cuff has been inflated to the initial pressure, the device proceeds to step 44 where the amplitude of the pressure pulses at that cuff pressure are measured. The values for these amplitudes as well as the cuff pressure are then stored together during this step. The cuff pressure is incremented (step 46) and the measurement and storage operation are repeated (step 48). At this point, a determination is made in step 50 as to whether the amplitudes of the pulses are increasing or decreasing.

If the pulse amplitudes are decreasing, it is an indication that the cuff pressure is already above the mean arterial pressure. Therefore, in step 49 a new cuff pressure, equivalent to the initial cuff pressure minus an arbitrary large drop, for example 50 mm Hg, is established and the steps of amplitude measurement followed by a pressure increment are repeated to see if the oscillations are increasing or decreasing. Again, it is determined in step 50 if the oscillations are increasing. Since the initial pressure was 70 mm Hg and the arbitrary drop was 50 mm Hg, it will be found that the pulse amplitudes are nearly always increasing since the cuff pressure is only 20 mm Hg. An increase in pulse amplitudes for increasing cuff pressure is an indication that the device is proceeding towards MAP.

If that arbitrary drop in the cuff pressure value is set at a smaller value, e.g. 25 mm Hg instead of 50 mm Hg, it is still possible for MAP to be below the cuff pressure. When this occurs, step 49 is repeated, but without modification the system still would not approach the correct setting because step 49 requires it to continue to return to a setting based on the initial pressure of 70 mm Hg, i.e. it would alternate between 70 and 45 mm Hg. In order to avoid this situation when smaller arbitary drops are made, step 49 is modified so that the pressure is set to the previous pressure minus the arbitary value, and not the initial pressure minus this value. Thus, in the example given the pressure would initially be 70 mm Hg, would drop to 45 mm Hg and then to 20 mm Hg.

Once it is found in step 50 that the amplitudes are increasing, the cuff pressure is continually incremented (step 52) and the amplitudes are measured and stored (step 54). At the completion of each measurement step 54 a decision step 56 is used to determine if the MAP criteria has been met. This criteria may be set in any convenient manner to determine the maximum amplitude of the pulses. One particularly useful technique is to require one lowered pulse amplitude after the occurrence of at least three increasing or level pulse amplitudes. Once this criteria has been met, MAP is recorded in step 58. Up to that time, however, the device continues to recycle, increasing the cuff pressure in increments and measuring the amplitudes of the resulting pulses.

In order to determine the systolic pressure, the cuff pressure continues to increase in increments (step 59) while the amplitudes are measured (step 60). After each such measurement, a decision is made in step 62 as to whether the systolic criteria has been met. Upon satisfying the criteria, the systolic pressure is recorded in step 64 and the previously recorded data is checked in decision step 66 to see if the diastolic pressure was found. The diastolic pressure, as previously noted, will be a cuff pressure below MAP. If such a pressure was previously found, it is recorded in step 68 and then the cuff is deflated to zero in step 70 while the measured values are read out, thus ending the measuring operation in step 72.

Figure 4A:
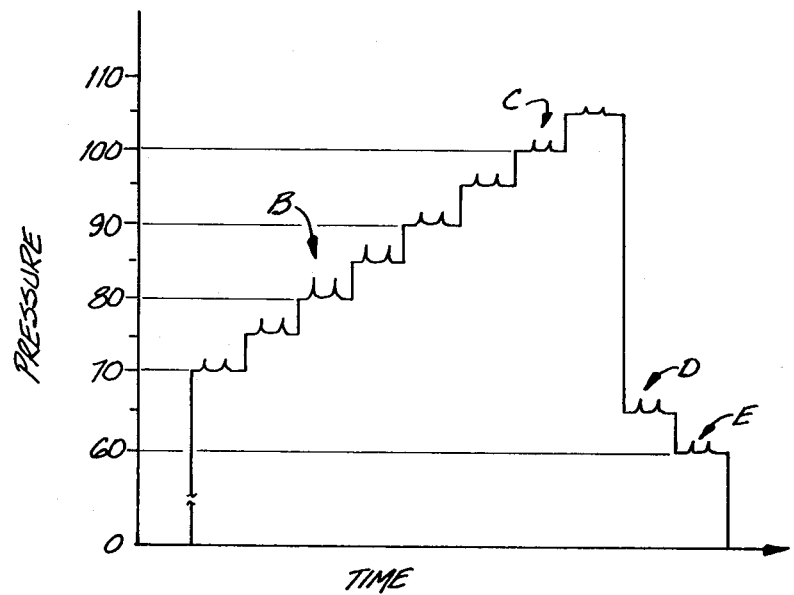
FIGS. 4a and 4b are graphs of cuff pressure and pulse amplitude, respectively, for a test subject having a low diastolic pressure.
Figure 4B:
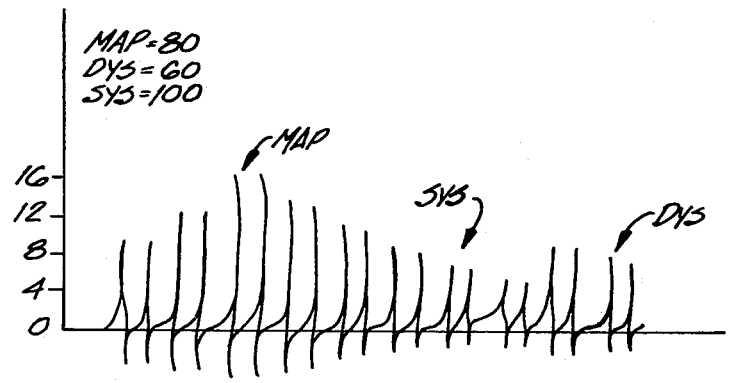
Figure 5A:
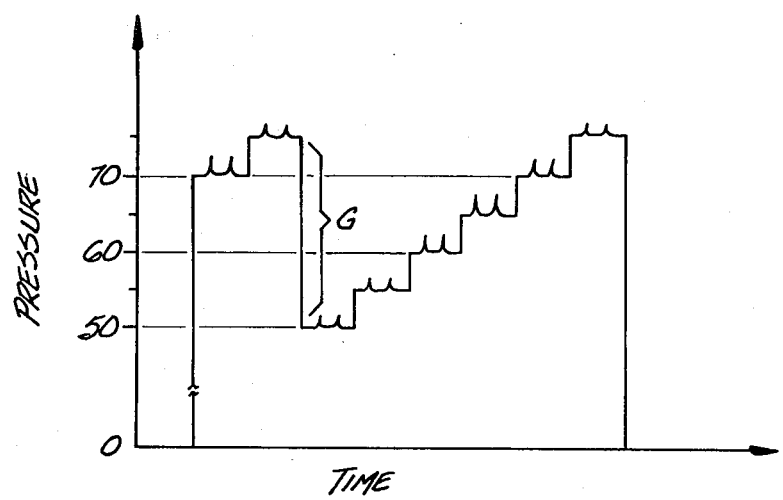
FIGS. 5a and 5b are graphs of cuff pressure and pulse amplitudes, respectively, for a test subject having both a low mean arterial pressure and a low diastolic pressure.
Figure 5B:
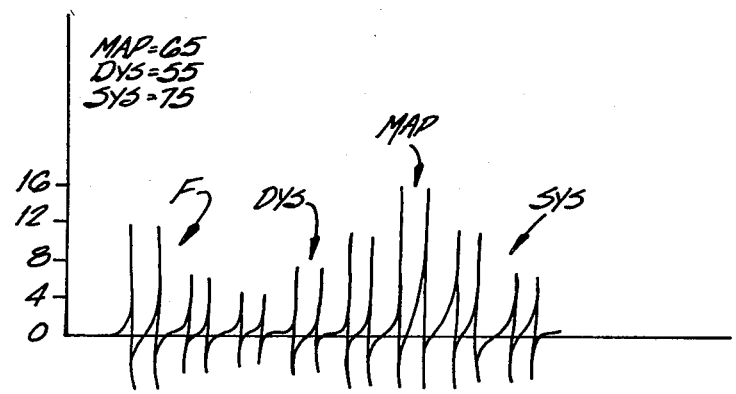

For a situation like that in FIGS. 4a and 4b, where it is determined that the diastolic pressure criteria cannot be met by the available data, the cuff pressure is decreased to the initial pressure minus one increment (step 61). Then the pulse amplitudes are measured in step 63 and are compared to the criteria for diastolic pressure in step 65. If that criteria is not met on the first attempt, the cuff pressure is decremented (step 67) and the measurement is repeated again until the criteria is met. When it is met, the diastolic pressure is recorded, the cuff pressure is reduced to zero and the process ends.

While suitable individual electronic components of both the analog and digital type can be used to implement the present invention, it is nevertheless a preferred embodiment of the present invention to reprogram a commercially-available model 845A DINAMAP ™ blood pressure monitor manufactured by Critikon Corp. of Tampa, FL. In order to modify it to operate in an adaptive manner according to the present invention, i.e. so that it may perform the operations shown in FIGS. 4 and 5, it is necessary to change the program in PROM 38 of the microprocessor in this unit according to the flow chart of FIG. 2. Such a program is reasonably within the capability of one skilled in the art and thus a program therefor is not listed herein.

While the present invention has been particularly shown and described with reference to a preferred embodiment thereof, it will be understood by those skilled in the art that various changes in form and details may be made therein without departing from the spirit and the scope of the invention.

We claim:

1. A method for automatically measuring blood pressure in a living animal test subject, comprising the steps of:
   (a) applying a predetermined initial pressure externally to the body of the test subject adjacent a blood vessel;
   (b) recording the value of the applied pressure and the amplitude of pressure pulses withing the blood vessel due to the operation of the heart of the test subject;
   (c) incrementally increasing the applied pressure at least once and repeating the recording step (b) after each increment;
   (d) if the amplitudes of the pulses increase with incremental increases of the applied pressure above the predetermined pressure and then decrease, (i) designating the applied pressure when the pulse amplitude is greatest as mean arterial pressure, (ii) designating as systolic pressure the applied pressure above mean arterial pressure where the pulse amplitude is a first fixed fraction of the amplitude at mean arterial pressure, and (iii) designating as diastolic pressure the applied pressure below mean arterial pressure at which the pulse amplitude is a second fixed fraction of the amplitude at mean arterial pressure;
   (e) if the amplitudes of the pulses first decrease with incremental increases of the applied pressure above the predetermined initial pressure, changing said applied pressure to a new applied pressure that is a certain amount below the predetermined initial pressure, and repeating steps (b)–(d) until mean arterial pressure and systolic pressure are determined;
   (f) halting the incremental changes in applied pressure after the determination of systolic, diastolic and mean arterial pressure; and
   (g) relieving the applied pressure.

2. A method according to claim 1 further including the steps of:
   (i) determining if the predetermined pressure was such that diastolic pressure cannot be designated in step (d),
   (ii) if diastolic pressure cannot be designated in step (d), changing the applied pressure to the predetermined pressure,
   (iii) incrementally decreasing the applied pressure by one step;
   (iv) successively recording the values of the applied pressure and the amplitude of the pulses, and further incrementally decreasing the applied pressure until diastolic pressure can be designated as the applied pressure at which the pulse amplitude is the second fixed fraction of the amplitude at mean arterial pressure.

3. A method according to claims 1 or 2 wherein said step of applying a predetermined initial pressure involves applying a pressure which is equivalent to a previously determined diastolic pressure with a fixed amount subtracted therefrom.

4. A method as claimed in claim 3 wherein the fixed amount is equal to a pressure of 15 millimeters of mercury.

5. A method as claimed in claims 1 or 2 wherein said certain amount is less than said predetermined initial pressure.

6. A method as claimed in claim 5 wherein said, predetermined initial pressure is 70 millimeters of mercury, said certain amount is 50 millimeters of mercury, and said incremental increases and decreases of applied pressure are in steps of about 5 millimeters of mercury.

7. A method as claimed in claims 1 or 2 further including after step (e) the steps of:
   (i) determining if, after execution of step (e), the amplitudes of the pulses continue to decrease with incremental increases of applied pressure above the new applied pressure,
   (ii) if it is found that the amplitudes continue to decrease, changing said new applied pressure to a further new pressure that is below the new applied pressure by the certain amount,
   (iii) repeating steps (b)–(d), and
   (iv) continuing to generate further new pressure levels by subtracting the certain amount from previous new pressures and repeating steps (b)–(d) until the pulse amplitudes increase for incremental increases of applied pressure above the new pressure level, or said new applied pressure is zero or less.

8. A method as claimed in claim 7 wherein the certain amount is 25 millimeters of mercury and said predetermined initial pressure is 70 millimeters of mercury.

9. Apparatus for automatically measuring blood pressure in a living animal test subject comprising:
   means for automatically applying a variable pressure externally to the body of the test subject adjacent a blood vessel;
   means for detecting the value of the applied pressure as well as the amplitude of pressure pulses within the blood vessel due to the operation of the heart of the test subject;
   means for storing in a correlated fashion the values of applied pressure and the amplitude of pressure pulses detected at those applied pressures;
   means for incrementally increasing the applied pressure in pressure increments from a predetermined pressure;
   means for determining the applied pressure at which the pulse amplitude is maximum and indicating that pressure as mean arterial pressure, and the applied pressures above and below mean arterial pressure at which the pulse amplitudes are certain fixed ratios of the pulse amplitude at mean arterial pressure and indicating them as systolic and diastolic pressure, respectively;
   means for detecting an increase or decrease in the pulse amplitudes prior to reaching the maximum pulse amplitude; and
   means for causing a fixed drop in the applied pressure, which is substantially larger than the incremental increases, when said means for detecting an increase or decrease detects a decrease in pulse amplitudes for increases in applied pressure immediately above the predetermined pressure.

10. Apparatus as claimed in claim 9 further including means for causing the applied pressure to return to the initial predetermined pressure and then incrementally decreasing when the means for determining and indicating is incapable of indicating the applied pressure below mean arterial pressure at which the pulse amplitudes are a certain fixed ratio because the initial predetermined pressure was too high.

11. Apparatus as claimed in claims 9 or 10 wherein (i) said means for applying pressures is a pump, (ii) said means for detecting pressure is a pressure transducer and an electrical peak-to-peak detector, and (iii) the means for storing, means for increasing the applied pressure, means for determining and indicating, means for detecting an increase or decrease, and means for causing are all a microprocessor.

* * * * *